(12) United States Patent
Beaudoin et al.

(10) Patent No.: US 6,990,431 B2
(45) Date of Patent: Jan. 24, 2006

(54) SYSTEM AND SOFTWARE TO MONITOR CYCLIC EQUIPMENT EFFICIENCY AND RELATED METHODS

(75) Inventors: Benoît Beaudoin, St-Hubert (CA); Jonathan Corriveau, Austin (CA)

(73) Assignee: Municipal and Industrial Data Labs, Inc., St. Hubert (CA)

( * ) Notice: Subject to any disclaimer, the term of this patent is extended or adjusted under 35 U.S.C. 154(b) by 0 days.

(21) Appl. No.: 10/875,740

(22) Filed: Jun. 23, 2004

(65) Prior Publication Data

US 2004/0260514 A1 Dec. 23, 2004

Related U.S. Application Data

(60) Provisional application No. 60/480,706, filed on Jun. 23, 2003.

(51) Int. Cl.
G06F 15/46 (2006.01)

(52) U.S. Cl. ............... 702/182; 702/33; 702/42; 700/130; 700/143; 700/206

(58) Field of Classification Search ............... 702/182, 702/33, 42, 185, 183; 700/130, 143, 206; 324/770, 71.3
See application file for complete search history.

(56) References Cited

U.S. PATENT DOCUMENTS

| | | |
|---|---|---|
| 4,142,238 A | 2/1979 | Brandt et al. |
| 4,194,178 A | 3/1980 | Dumbeck |
| 4,455,870 A | 6/1984 | Jorritsma |
| 4,525,763 A | 6/1985 | Hardy et al. |
| 4,581,711 A | 4/1986 | Hirata et al. |
| 4,669,308 A | 6/1987 | Jorritsma |
| 4,707,796 A | 11/1987 | Calabro et al. |
| 4,821,580 A | 4/1989 | Jorritsma |
| 4,839,830 A | 6/1989 | Amey et al. |
| 4,924,404 A | 5/1990 | Reinke, Jr. |
| 4,999,117 A | 3/1991 | Palmu et al. |
| 5,067,099 A | 11/1991 | McCown et al. |
| 5,070,468 A | 12/1991 | Niinomi et al. |
| 5,081,598 A | 1/1992 | Bellows et al. |
| 5,099,436 A | 3/1992 | McCown et al. |
| 5,103,409 A | 4/1992 | Shimizu et al. |
| 5,130,936 A | 7/1992 | Sheppard et al. |
| 5,132,920 A | 7/1992 | Bellows et al. |
| 5,134,574 A | 7/1992 | Beaverstock et al. |
| 5,182,951 A | 2/1993 | Jorritsma |
| 5,189,350 A | 2/1993 | Mallett |
| 5,193,143 A | 3/1993 | Kaemmerer et al. |
| 5,313,842 A | 5/1994 | Marsh et al. |
| 5,351,247 A | 9/1994 | Dow et al. |

(Continued)

Primary Examiner—Bryan Bui
Assistant Examiner—Hien Vo
(74) Attorney, Agent, or Firm—Bracewell & Giuliani LLP

(57) ABSTRACT

Systems, software and methods of embodiments of the present invention are able to monitor and evaluate the efficiency of an equipment operating cyclically to displace a variable workload without any input from an operator or the use of specialized metering equipment. A cyclic equipment efficiency monitoring system includes a workload calculator for determining the workload being accumulated and displaced through a system having an equipment operating cyclically by using the equipment status signals and clock signals. An efficiency calculator extracts a probable efficiency. The accuracy is increased by a self adjustment mechanism. A data quality certification mechanism verify that workload and efficiency values are within possible range and declare alarm conditions, high variation conditions or maintenance conditions. A variation alarm gate generates an alarm if the workload or the efficiency are outside acceptable limits.

11 Claims, 18 Drawing Sheets

U.S. PATENT DOCUMENTS

| | | | |
|---|---|---|---|
| 5,385,056 A | 1/1995 | Marsh et al. |
| 5,394,543 A | 2/1995 | Hill et al. |
| 5,404,503 A | 4/1995 | Hill et al. |
| 5,461,329 A | 10/1995 | Linehan et al. |
| 5,467,650 A | 11/1995 | Cushing |
| 5,485,491 A | 1/1996 | Salnick et al. |
| 5,488,697 A | 1/1996 | Kaemmerer et al. |
| 5,497,664 A | 3/1996 | Jorritsma |
| 5,502,374 A | 3/1996 | Cota |
| 5,511,004 A | 4/1996 | Dubost et al. |
| 5,519,300 A | 5/1996 | Leon et al. |
| 5,521,482 A | 5/1996 | Lang et al. |
| 5,523,701 A | 6/1996 | Smith et al. |
| 5,528,516 A | 6/1996 | Yemini et al. |
| 5,576,632 A | 11/1996 | Petsche et al. |
| 5,597,960 A | 1/1997 | Beaudoim |
| 5,629,870 A | 5/1997 | Farag et al. |
| 5,661,386 A | 8/1997 | Kueck et al. |
| 5,661,668 A | 8/1997 | Yemini et al. |
| 5,675,497 A | 10/1997 | Petsche et al. |
| 5,680,025 A | 10/1997 | Bowers, III et al. |
| 5,705,989 A | 1/1998 | Cota et al. |
| 5,726,911 A | 3/1998 | Canada et al. |
| 5,742,500 A | 4/1998 | Irvin |
| 5,808,846 A | 9/1998 | Holce et al. |
| 5,831,174 A | 11/1998 | Beaudoin |
| 5,854,424 A | 12/1998 | Jorritsma |
| 5,893,047 A * | 4/1999 | Gimblett et al. ............... 702/33 |
| 5,991,707 A * | 11/1999 | Searles et al. ............... 702/185 |
| 6,005,760 A | 12/1999 | Holce et al. |
| 6,017,143 A | 1/2000 | Eryurek et al. |
| 6,144,924 A | 11/2000 | Dowling et al. |
| 6,172,509 B1 | 1/2001 | Cash et al. |
| 6,178,393 B1 | 1/2001 | Irvin |
| 6,192,325 B1 | 2/2001 | Piety et al. |
| 6,199,018 B1 | 3/2001 | Quist et al. |
| 6,203,280 B1 | 3/2001 | Van Zyl |
| 6,260,004 B1 | 7/2001 | Hays et al. |
| 6,297,742 B1 | 10/2001 | Canada et al. |
| 6,308,138 B1 | 10/2001 | Jones et al. |
| 6,330,525 B1 | 12/2001 | Hays et al. |
| 6,331,821 B1 | 12/2001 | Holce et al. |
| 6,338,029 B1 | 1/2002 | Abbata et al. |
| 6,377,430 B2 | 4/2002 | Holce et al. |
| 6,397,114 B1 | 5/2002 | Eryurek et al. |
| 6,411,908 B1 | 6/2002 | Talbott |
| 6,442,511 B1 | 8/2002 | Sarangapani et al. |
| 6,532,426 B1 | 3/2003 | Hooks et al. |
| 2002/0046004 A1 | 4/2002 | Cusumano et al. |
| 2003/0009311 A1 | 1/2003 | Ushiku et al. |

\* cited by examiner

CONVEYOR

LIFT STATION

WATER TOWER

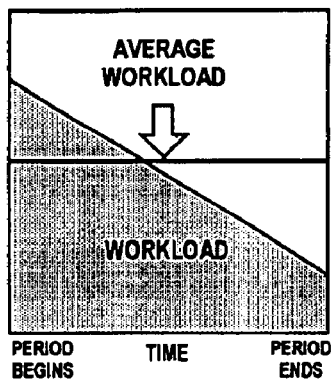
FIG. 12A.
CONSTANT WORKLOAD
FIG. 12B.
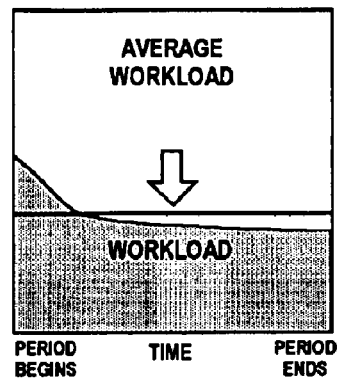
LOCK-ON PHENOMENON
INCREASING WORKLOAD'
THEN ALMOST EQUAL
TO EQUIPMENT'S THROUGHPUT.
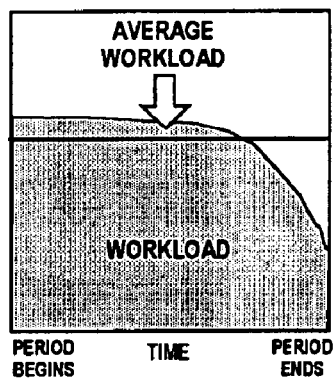
FIG. 12C.
LOCK-ON PHENOMENON
WORKLOAD ALMOST EQUAL
TO EQUIPMENT'S THROUGHPUT,
THEN DECREASING WORKLOAD.

SYSTEM AND SOFTWARE TO MONITOR CYCLIC EQUIPMENT EFFICIENCY AND RELATED METHODS

RELATED APPLICATIONS

This patent application claims priority to U.S. Provisional Patent Application Ser. No. 60/480,706 titled "System and Software to Monitor Cyclic Equipment Efficiency and Related Methods" filed on Jun. 23, 2003, and which is incorporated herein by reference in its entirety.

BACKGROUND OF THE INVENTION

1. Field of the Invention

The present invention is related to systems, software, and methods of monitoring equipment and, more particularly, systems software and methods related to cyclic equipment.

2. Discussion of Related Art

Over the years, it has becomes increasingly difficult to evaluate to establish the proper time interval for scheduling preventive maintenance on process equipment. Also, many systems describe what to do when equipment needs maintenance, but few systems actually provide ways to detect deteriorating equipment. Various approaches of evaluating when to schedule maintenance or replacement of the process equipment have prevailed such as using experience with the specific type of equipment, prior practices of others, the users best guess, the manufacturer's recommendations, or to simply do nothing and repair the equipment when it breaksdown. This latter approach is based on an outdated hypothesis which states that it is better to operate equipment until it fails than to accept the maintenance and penalty costs of shutting down prematurely. Other approaches have weighed the cost of premature overhaul of the equipment against the cost of continuing operation and risking unexpected early failure. An even more recent approach has been toward using normal statistical distribution models with data processed by computer programs to determine when to perform scheduled maintenance. Using these normal statistical distribution models and other similar statistical methodologies, it is possible to predict the probability of an "average" piece of equipment failing prior to, on, or after a certain time such that preventive maintenance can be performed prior to probable equipment failure. Statistically, however, many individual pieces of equipment will survive for a longer period but are overhauled prematurely because this methodology and various other statistical methods apply to populations of the same type of equipment and do not actually examine each individual piece of equipment.

An example of this type of system is a conveyor displacing its load only when there is enough weight accumulated on the conveyor and runs until the load gets to a lower weight (See Prior Art FIG. 1). The conveyor is activated by the scale until the weight goes down to a predetermined lower weight. Another example of this type of system is a pump starting only when there is enough liquid accumulated in a tank or a well and runs until a lower level is reached, as seen in lift stations (See Prior Art FIG. 1B). Yet Another example of this type of system is a pump used to fill up a water tower or a tank (See Prior Art FIG. 1C). When the water pressure or level gets to a low point, a pump is activated until the water tower is filled up to a higher pressure or a higher level.

Even more recently, a trend has been toward foregoing statistical methodologies in favor of measuring various equipment parameters of the individual piece of equipment. Most systems made to detect abnormal equipment behaviours use one to many sensors of different type related to the equipment being monitored to supply processed data into usable maintenance information. For example, U.S. Pat. No. 4,707,796, by Calabro et al., titled "Reliability and Maintainability Indicator" describes an attempt to predict the remaining time of operation of a piece of equipment before it would fail by measuring key parameters of the equipment monitored with applicable transducers over time which are correlated and analyzed by a micro-processor based computer.

For many systems, the information supplied must be compared to other information from the same source or other sources to evaluate the deterioration of the equipment being monitored. For example, U.S. Pat. No. 6,308,138B1, by Jones et al., titled "Diagnostic Rule Based Tool Condition Monitoring System" describes a system to monitor various characteristics of the power consumption of a tool and diagnoses the condition of the tool based upon the various characteristics with respect to a Rule base developed from an examination of the same characteristics of a tool of known condition. In U.S. Pat. No. 6,442,511B1, by Sarangapani et al., titled "Method and Apparatus for Determining the Severity of a Trend toward an Impending Machine Failure and Responding to the Same" describes determining a failure trend based on a set of normal operating conditions for the machine by determining the slope value for the typical failure trend and slope value for the trend toward the impending machine failure based on a weighted value of various sensed machine parameters. Also for example, U.S. Pat. No. 6,411,908, by Talbott, titled "Condition-Based Prognosis for Machinery" describes a method for estimating the remaining life in an operating machine that uses condition-based data histories of same-type machines situated in same-type operational environments that have all failed according to the same failure mode, whereby the data is obtained from end-users who have monitored their machines with the appropriate sensor technology and have performed autopsies on the failed machines to verify the failure mode of the machines.

In other systems, like for most flow related systems, the user must further evaluate the data to extract maintenance information like for most known flow related systems. For example, U.S. Pat. No. 5,991,707, by Searies et al., titled "Method and System for Predictive Diagnosing of System Reliability Problems And/or System Failures in a Physical System" describes an attempt to diagnose system reliability problems or system failure through identification of errant fluctuations in one or more operating parameters of a physical system. A datastream of parameter values are divided into one or more sets and the sets are associated into one or more sensors to examine statistically for conditions that indicate whether or not the values are within operating range. Many systems describe what to do when equipment needs maintenance. Only few systems actually provide ways to detect deteriorating equipment.

Applicants have recognized that equipment made to operate at a constant speed on a constant workload often deteriorates as a function of a single variable, namely time. It becomes difficult to evaluate the speed of deterioration with a perpetual variable workload and equipment operating cyclically to displace the accumulated workload. Usually, metering equipment for level, flow, pressure, current, or vibration are added to a process to evaluate the efficiency or speed of deterioration on equipment within the process. Sometimes, the operator must supply operating parameters such as regime, weight or volume to calculate a meaningful value that may indicate the performance of the equipment. If the metering equipment is defective or the operator's input is inaccurate, then the evaluation would be meaningless.

Applicants advantageously have recognized a need to evaluate the efficiency of equipment operating cyclically to displace a variable workload without any input from an operator or the use of sensors or specialized metering equipment.

SUMMARY OF THE INVENTION

In view of the foregoing, embodiments of systems, software and methods of the present invention advantageously are able to monitor and evaluate the efficiency of equipment operating cyclically to displace a variable workload without any input from an operator or the use of specialized metering equipment, thereby reducing the risk of using wrong parameters. Advantageously, embodiments of a system, software, and methods to monitor cyclic equipment efficiency according to the present invention can only require the status of operation of the equipment and time of change of the status, thereby not requiring use or installation of sensors.

Accordingly, several additional advantages of embodiments of a system, software, and methods of the present invention are:
a) to provide embodiments of a cyclic equipment efficiency monitoring system, software, and methods that can evaluate the efficiency of an equipment, without removing it or stopping it from its normal operation;
b) to provide embodiments of a cyclic equipment efficiency monitoring system, software, and methods that can compare the workload being displace to the work done by an equipment;
c) to provide embodiments of a cyclic equipment efficiency monitoring system, software, and methods that can detect high variation equipment efficiency and declare alarms;
d) to provide embodiments of a cyclic equipment efficiency monitor that can detect over maximum workload conditions and declare alarms;
e) to provide embodiments of a cyclic equipment efficiency monitoring system, software, and methods that can detect under minimum workload conditions and declare alarms; and
f) to provide embodiments of a cyclic equipment efficiency monitoring system, software, and methods that can detect when equipment is receiving maintenance.

More particularly, an embodiment of a cyclic equipment efficiency monitoring system, for example, can include a workload calculator to determine the workload being accumulated and displaced through a system having equipment operating cyclically by using the equipment status signals and clock signals. The system also includes an efficiency calculator to extract a probable efficiency. The accuracy of the system can be increased by a self adjustment mechanism. A data quality certification mechanism of the system verifies that workload and efficiency values are within a possible range and declares alarm conditions, high variation conditions or maintenance conditions. The system can also include a variation alarm gate to generate an alarm if the workload or the efficiency are outside acceptable limits.

Embodiments of a system, software, and methods of the present invention advantateously evaluate the efficiency of equipments operating within cyclic systems. Applicants have recognized that the "efficiency" and the "workload" are not a weight, a flow, a volume, a pressure or anything alike, but "efficiency" and "workload" are information that can be used for maintenance purposes to evaluate the speed of deterioration of an equipment without using any specialized sensors or requiring human inputs.

The embodiments of a cyclic equipment efficiency monitoring system, software, and related methods of the present invention also can, for example, include a computer having memory defining an equipment efficiency monitoring server, efficiency monitoring software stored in the memory of the server, an area network in communication with the server, and an equipment monitor sensor, e.g., a current sensor or other transducer, positioned remote from the server, in communication with the area network, and in communication with a cyclical equipment device or system to be monitored to sense "on" and "off" status of the cyclical equipment device and time that the cyclical equipment device is in the on-status and in the off-status. The equipment monitor sensor can also sense a cyclical equipment device identifier associated with the cyclical equipment device so that the cyclical equipment device being sensed by the equipment monitor sensor is specifically identified for monitoring.

The efficiency monitoring software, for example, includes a workload calculator responsive to the efficiency monitor sensor to calculate the workload of the cyclical equipment device and an efficiency calculator responsive to the workload calculator to determine the efficiency of the cyclical equipment device. The software can also include variations determiner responsive to the workload calculator and the efficiency calculator to determine a variation in the workload and the efficiency and a variation alarm initiator responsive to the variation determiner to initiate an alarm condition indicating that an abnormal variation has occurred. The variation determiner, for example, can include a tolerance comparator to compare a determined tolerance value with an acceptable value and a tolerance modifier responsive to the tolerance comparator and the efficiencies determined by the efficiency calculator to modify or adjust the tolerance. The tolerance comparator also can be in communication with the workload calculator to further enhance workload calculations when a potential abnormal variation is determined.

Advantageously, an embodiment of the present invention monitors a cyclical equipment device, such as, a conveyor, a lift station, a water tower, or any other cyclical equipment. In an embodiment of the present invention, the system and software advantageously operate to monitor workload and efficiency, without the need for continuous operator input, complex sensor input, or specialized metering equipment, and determines deterioration within the equipment being monitored. Rather than special sensors, meters, or continuous operator input, the system can utilize equipment status signals, e.g., on/off, and clock signals, e.g., length of time on and/or off, to effectively monitor the equipment. Also, the equipment status and time can be stored in the memory of the server, if desired. The system does not need to sense or measure speed, volume, pressure, or weight per unit time. Instead, calculations of workload and efficiency are based on predetermined assumptions about the equipment from which the workload, efficiencies, and other calculations from status and time can be made. The system, software, and methods can evaluate the efficiency of the equipment, without removing it or stopping it from its normal operation. The system, software, and methods can also compare the workload being displaced to the work done by the equipment and can detect a high variation in equipment efficiency and declare alarms. Advantageously, the cyclic equipment efficiency monitoring system, software, and methods can detect over maximum and under minimum workload conditions and declare alarms, respectively. Advantageously, in an embodiment of the present invention, the cyclic equipment efficiency monitoring system, software, and methods can detect when the equipment is receiving maintenance.

BRIEF DESCRIPTION OF THE DRAWINGS

Some of the advantages and features of the present invention having been stated, others will become apparent as the description proceeds when taken in conjunction with the accompanying drawings, in which:

FIG. 12A is a graph of a cyclic equipment efficiency monitoring system with a work-load accumulation period and equipment-in-operation period according to an embodiment of the present invention;

FIG. 12B is a graph of a cyclic equipment efficiency monitoring system with a work-load accumulation period and equipment-in-operation period according to an embodiment of the present invention;

FIG. 12C is a graph of a cyclic equipment efficiency monitoring system with a work-load accumulation period and equipment-in-operation period according to an embodiment of the present invention;

DETAILED DESCRIPTION

The present invention now will be described more fully hereinafter with reference to the accompanying drawings in which illustrated embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. Like numbers refer to like elements throughout.

Figure 1A:
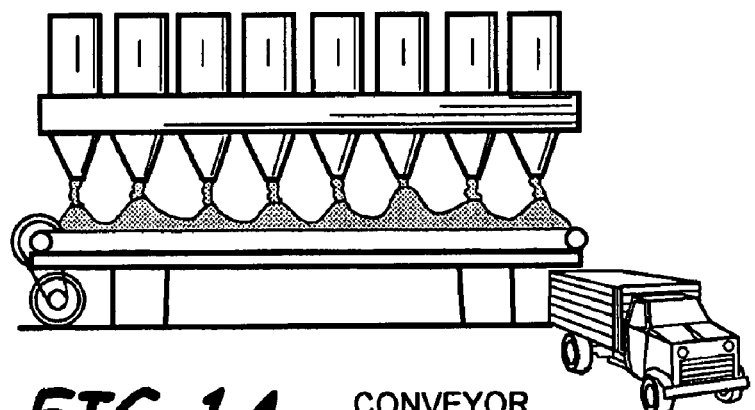
FIG. 1A is an environmental view of a system having cyclic equipment in the form of a conveyor having with a work-load accumulation period and an equipment-in-operation period according to the prior art.
Figure 1B:
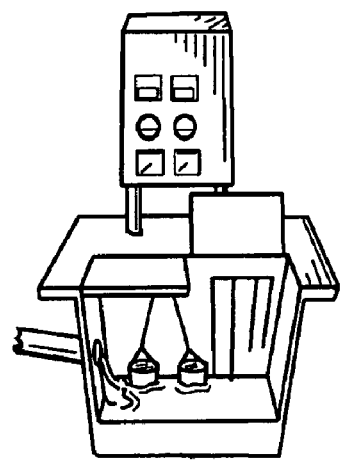
FIG. 1B is an environmental view of a system having cyclic equipment in the form of a lift station having a work-load accumulation period and an equipment-in-operation period according to the prior art.
Figure 1C:
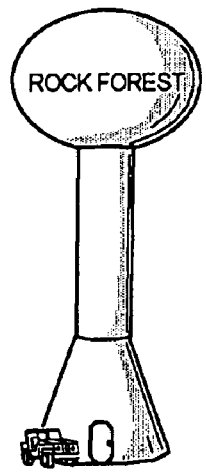
FIG. 1C is an environmental view of a system having cyclic equipment in the form of a water tower having a work-load accumulation period and an equipment-in-operation period according to the prior art.
Figure 2:
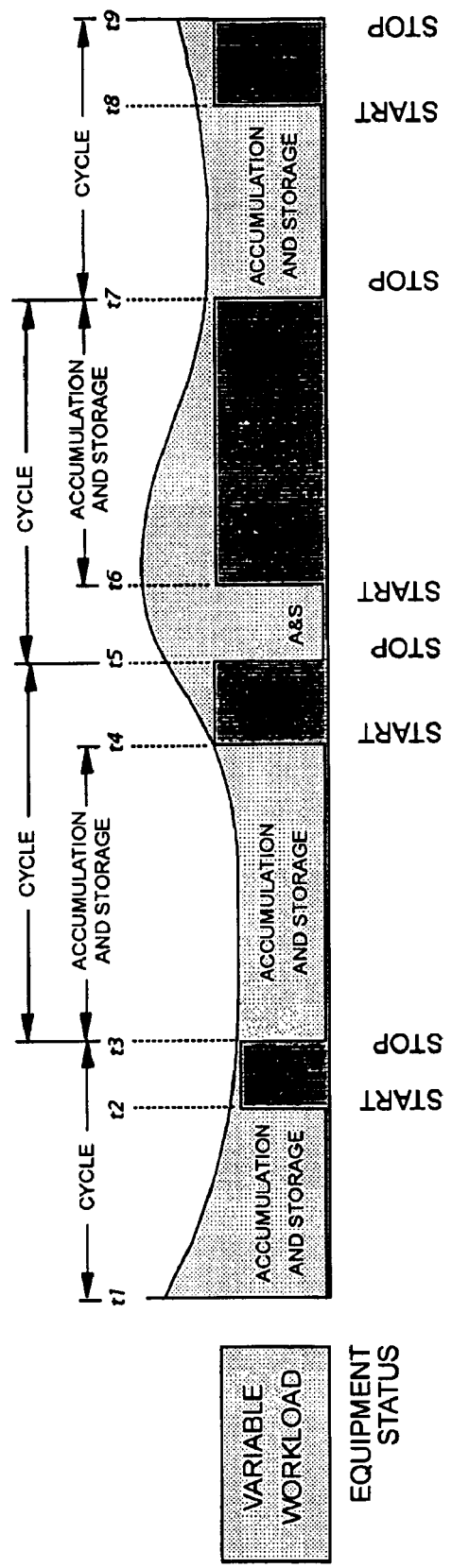
FIG. 2 is a graph of a cyclic equipment efficiency monitoring system with a work-load accumulation period and an equipment-in-operation period, according to an embodiment of the present invention.

FIG. 2 shows a graph of a method of monitoring a cyclic system 20 (See also FIG. 3) with a workload-accumulation-period and an equipment-in-operation period. Usually, cyclic systems accumulate a specific workload, such as a specific weight or volume, and then start the equipment until the full cycle accumulated workload is displaced, as showed in black. The gray or lighter shaded area shows a perpetual variable workload entering the cycling system, even when the equipment operates. The time of operation of the equipment is proportional to the unknown perpetual variable workload entering the storage area while the equipment is in operation and the variable efficiency of that equipment.

Embodiments of a system, software, and methods of the present invention cannot generate a weight per time or a volume per time (flow), but the workload and efficiency calculated by these embodiments can be multiplied by a weight, a volume, a pressure or another meaningful value to generate an even more useful data.

In a cyclical equipment device or system such as lift pump station, for example, an unknown and variable flow of liquid such as water constantly fills a well. When the liquid reaches the start level, a pump starts. When the liquid reaches the stop level, the pump stops. Correspondingly, until now, the only way to evaluate the throughput of the pump was to install:

a) a flow meter on the pump;
b) a pressure meter;
c) a volumetric flow meter and expecting the operator to supply an accurate volume and using level detection apparatus;
d) a current transducer; or
e) other similar sensing devices.

The operating time of the pump cannot be used to evaluate the equipment because the workload is always unknown and varies constantly. Until now, there was no way to evaluate the efficiency over time (or speed of deterioration) of equipment without inputs from an operator or the installation of specialized meters.

As illustrated in FIGS. 3–16 and as described herein, embodiments of a cyclic equipment efficiency system 20, software, and methods are provided and can use equipment status signals and clock signals that are recorded in memory before being used as input to an efficiency calculator 25, which calculates the perpetual variable workload and the equipment's efficiency. The equipment's efficiency within a cycle equals the accumulated workload displaced divided by the time of displacement by the equipment plus the average incoming variable workload for that time. The workload must be known to calculate the efficiency. To achieve the maximum workload and efficiency accuracy for a system, the following assumptions can be made:

a) The efficiency of an equipment varies slowly over time, unless an abnormal condition occurs;
b) The workload can vary rapidly; therefore the difference between reality and the calculated workload can be high;
c) The average of many calculated $\overline{Efficiency}$ over many cycles ($\overline{\overline{Efficiency}}$) is usually accurate, unless an abnormal condition occurs;
d) The real efficiency for an equipment is somewhere between $\overline{Efficiency}$ and $\overline{\overline{Efficiency}}$, unless an abnormal condition occurs; and
e) The $\overline{\overline{Efficiency}}$ is influenced by the average accumulated workload for the period at which $\overline{\overline{Efficiency}}$ is calculated.

In such a system, for example, a clock generates a time stamp at which the equipment status is changing. The equipment status is also used to identify the equipment for which an efficiency is calculated and its associated time stamp. The time stamp and the equipment status can optionally be recorded in a data storage memory for later processing.

Figure 3:
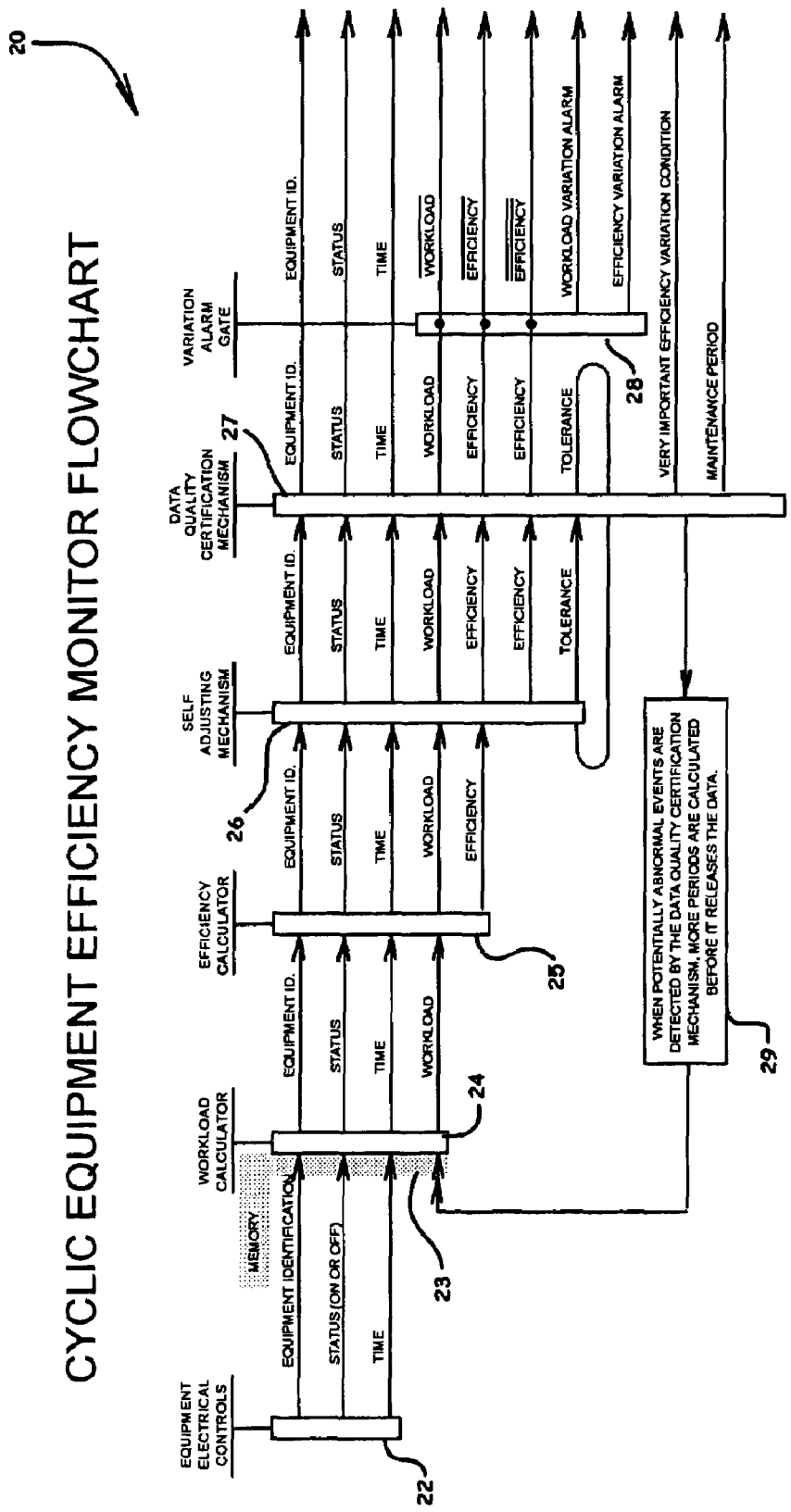
FIG. 3 is a flowchart of a cyclic equipment efficiency monitor according to an embodiment of the present invention.

FIG. 3, for example, shows a flowchart of a cyclic equipment efficiency system 20 and software to monitor efficiency of cyclic equipment. The equipment electrical control 22 generates a status for the equipment in operation. This can be a contact closing or opening, a current being generated, or anything that changes state at the same time as the equipment. The equipment generating the status (like a relay) also represents an identification of the equipment. This is useful when the cyclic equipment efficiency system 20 monitors more than one piece of equipment within a system. A data logging apparatus, e.g., memory or other data logger as understood by those skilled in the art, is used to add and record the time at which the change of status occurs. The equipment identification, its status and time of change of status are recorded in memory 23. A workload calculator 24 analyzes these three pieces of data and generates a Workload. An efficiency calculator 25 analyzes these four pieces of data and generates an Efficiency. A variation determining self-adjusting mechanism 26 analyses these five pieces of data and generates a more accurate Efficiency and a Tolerance representing what is normal or abnormal for this specific cyclic system. The Data Quality Certification Mechanism analyses these seven pieces of data and confirms the accuracy of the data, adjusts the Tolerance, can declare a "very important efficiency variation condition" or alarm and can declare a Maintenance Period being analyzed. When potentially abnormal events are detected, more periods are calculated before the data goes to the variation alarm initiator 28 or gate. The variation alarm initiator 28 or gate analyzes these seven pieces of data less the Tolerance and can generate a "workload variation alarm" and an "efficiency variation alarm."

Figure 4A:
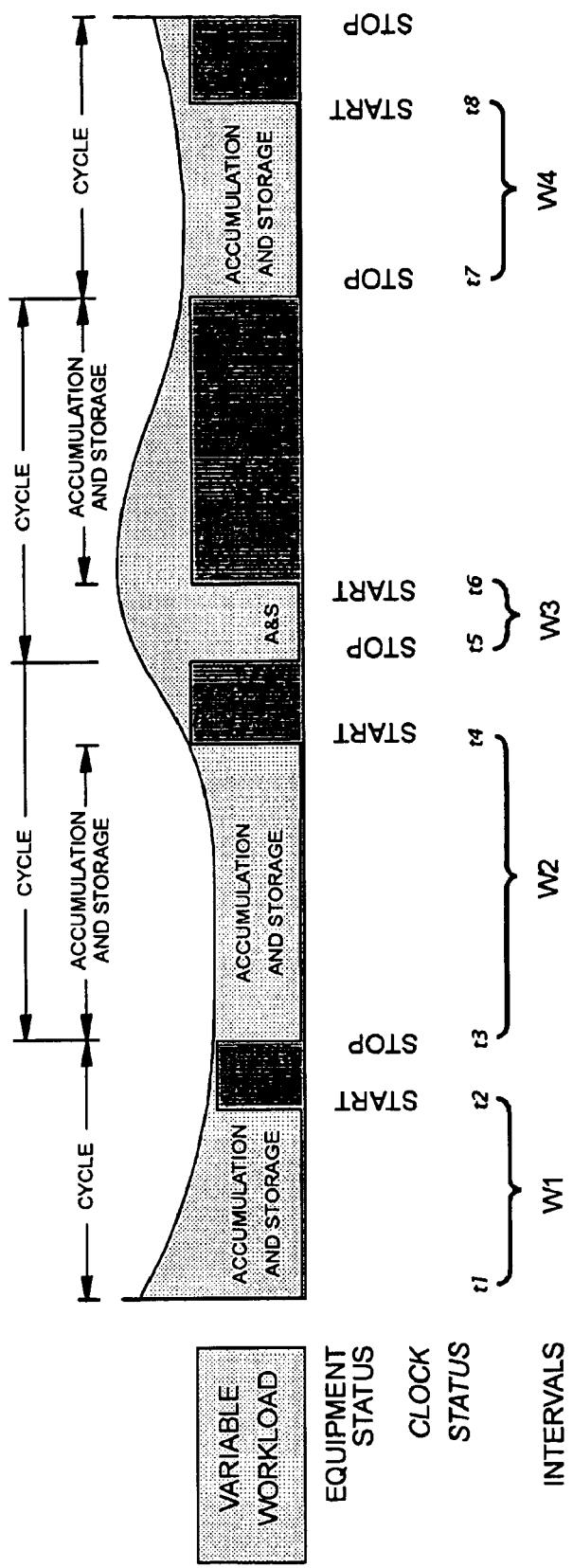
FIG. 4A is a graph of a cyclic equipment efficiency monitoring system with a work-load accumulation period and equipment-in-operation period according to an embodiment of the present invention.
Figure 4B:
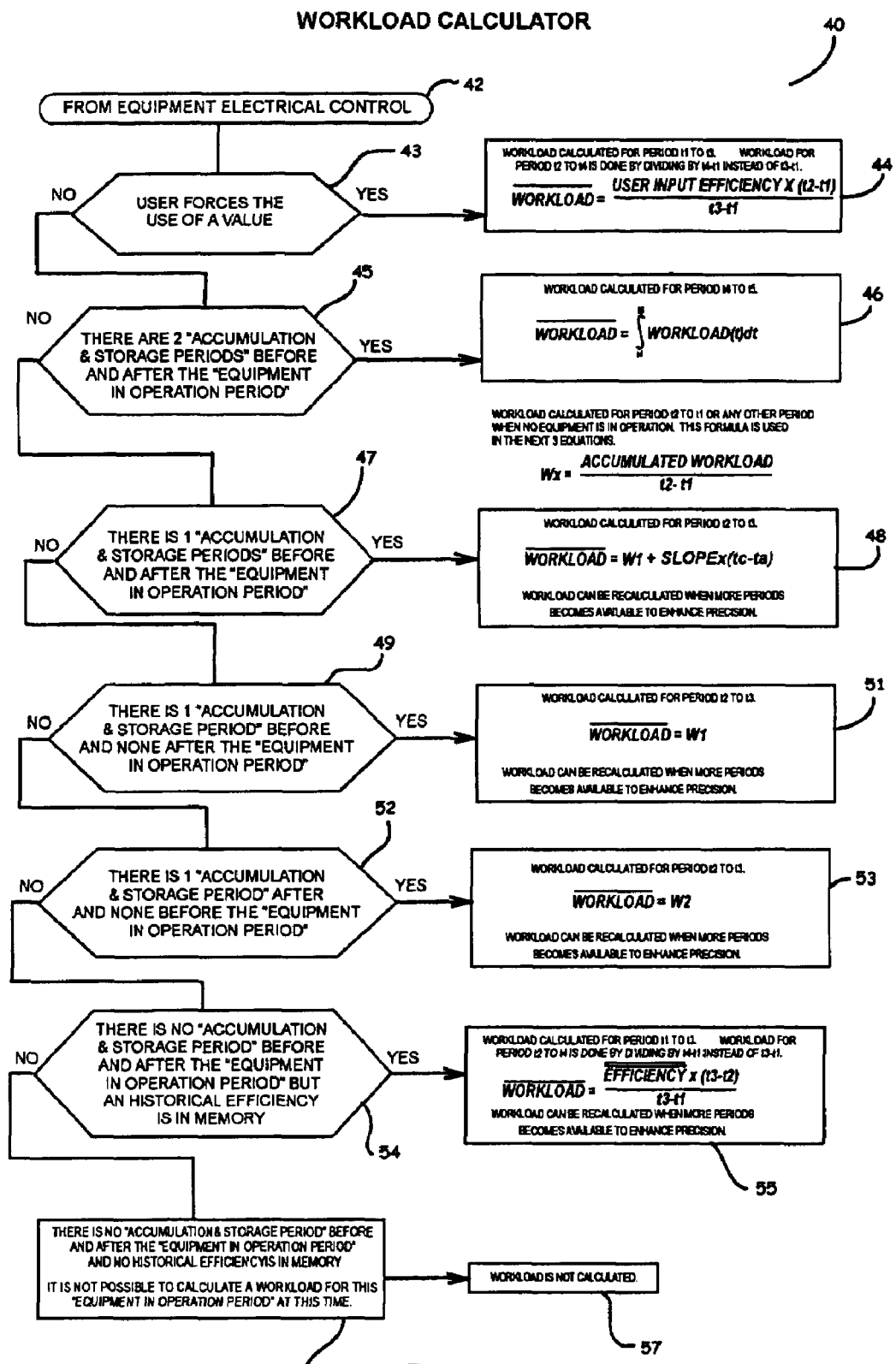
FIG. 4B is a flowchart of a cyclic equipment efficiency monitoring system with a work-load accumulation period and equipment-in-operation period according to an embodiment of the present invention.

As perhaps best shown in FIG. 4, the workload calculator includes a plurality of algorithms, the most efficient of which is preferably selected to calculate average variable workload. The workload calculator 24 includes several standard equations that will be referenced throughout.

Equation 1. The average variable workload for a period not having equipment in operation equals the accumulated workload divided by the duration of the period.

$$\overline{Workload} = \frac{\text{Accumulated workload}}{t2 - t1}$$

When a formula requires many workloads, then Wx represents the average workload for the period starting at $T_{beginning}$ and ending at $T_{end}$.

$$Wx = \frac{\text{Accumulated workload}}{t_{end} - t_{beginning}}$$

The accumulated workload cannot be known so 1 is used to simplify all calculation. Doing this means that the "workload" and "efficiency" calculated within a period can only be compared to other workloads or efficiencies calculated for the same type of period. The equipment's efficiency is equal to the accumulated workload divided by the time of operation of the equipment plus the incoming workload for that period.

$$\text{Efficiency} = \frac{\text{Accumulated workload}}{\text{Time of operation of the equipment}} + \overline{Workload}$$

The workload for a period having running equipment equals the equipment's efficiency less the accumulated workload divided by the time of operation of the equipment.

$$\text{Workload} = \text{Efficiency} - \frac{\text{Accumulated workload}}{\text{Time of operation of the equipment}}$$

To calculate either Workload or Efficiency, one or the other must be known or assumed. The accuracy of the equation is proportional to the assumed value. The goal is to get the potentially most accurate to calculate the other with it.

Cycle's average variable workload = $\frac{\text{Equipment's efficiency} \times \text{Equipment's time of operation}}{\text{time duration of the cycle}}$  Equation 2.

An unknown and invariable cumulative work (under normal conditions) accumulates and is stored in the "accumulation and storage" period. The time it takes to do this is also known. Because cumulative work is constant and the time is extremely accurate, it can be assumed that the average workload for the "accumulation and storage" period is also extremely accurate.

Average variable workload in the "accumulation and storage" period = $\frac{\text{accumulated work}}{\text{time of period}}$  Equation 3.

The average workload calculated for the "accumulation and storage" period can be used to estimate accurate workloads for all other periods using simple to complex statistical analysis. The assumed workloads are then used to calculate the equipment's efficiency. Sometimes, historical equipment efficiency can be used to calculate the workload. So, based on the assumed most accurate available data, the cyclic efficiency monitor switches between multiple algorithms to extract the most accurate values. The following paragraph "A to F" are elements of the "Workload Calculator" which supplies the most accurate workload available at this point in the process using the appropriate Workload algorithm.

A period starts and ends by any change of state of an equipment such as the start and stop of an equipment. In FIG. 4, t1 to t9 represents change of states of the equipment. A cycle starts and ends by the same change of state of an equipment like when an equipments start and the next time the same equipment starts. In FIG. 4, t1, t3, t5, t7 and t9 represents the beginning of a cycle. Each period is calculated using one of the following algorithms within the cyclic equipment efficiency monitor in the following order:

Step A:

$$\overline{\text{Workload}} = \frac{\text{User input efficiency} \times (t2 - t1)}{t3 - t1}$$

Figure 5:
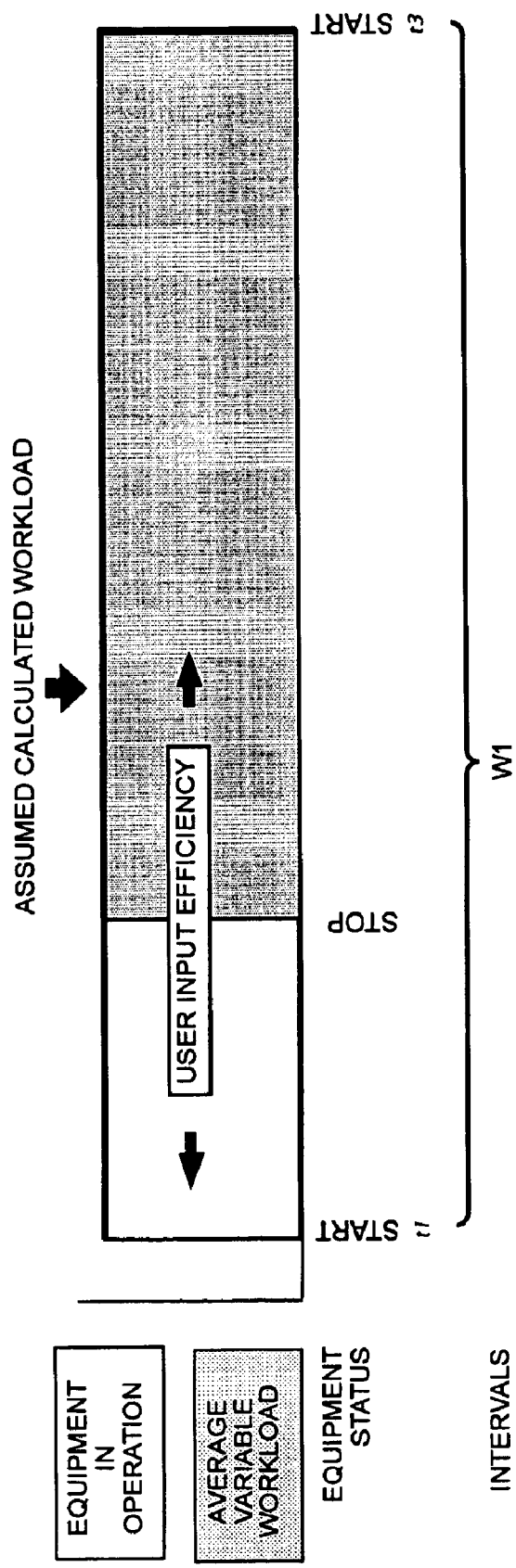
FIG. 5 is a graph of a cyclic equipment efficiency monitoring system with a work-load accumulation period and equipment-in-operation period according to an embodiment of the present invention.

Step A:

When Equation 3 cannot be used immediately before or after a period in which the equipment is in operation and an efficiency proportional to the manufacturer's design equipment throughput is known, then the user entered known equipment efficiency multiplied by the time of operation of the equipment for a period within a cycle divided by the time of the cycle gives the average variable workload within the cycle. This formula can also be used, even if Equation 3 can be used immediately before and/or after a period in which the equipment is in operation if the user thinks the operational condition of the system requires this. Therefore, if the operator enters a predetermined workload for a period, then the efficiency is calculated using this workload (FIG. 5).

Figure 6:
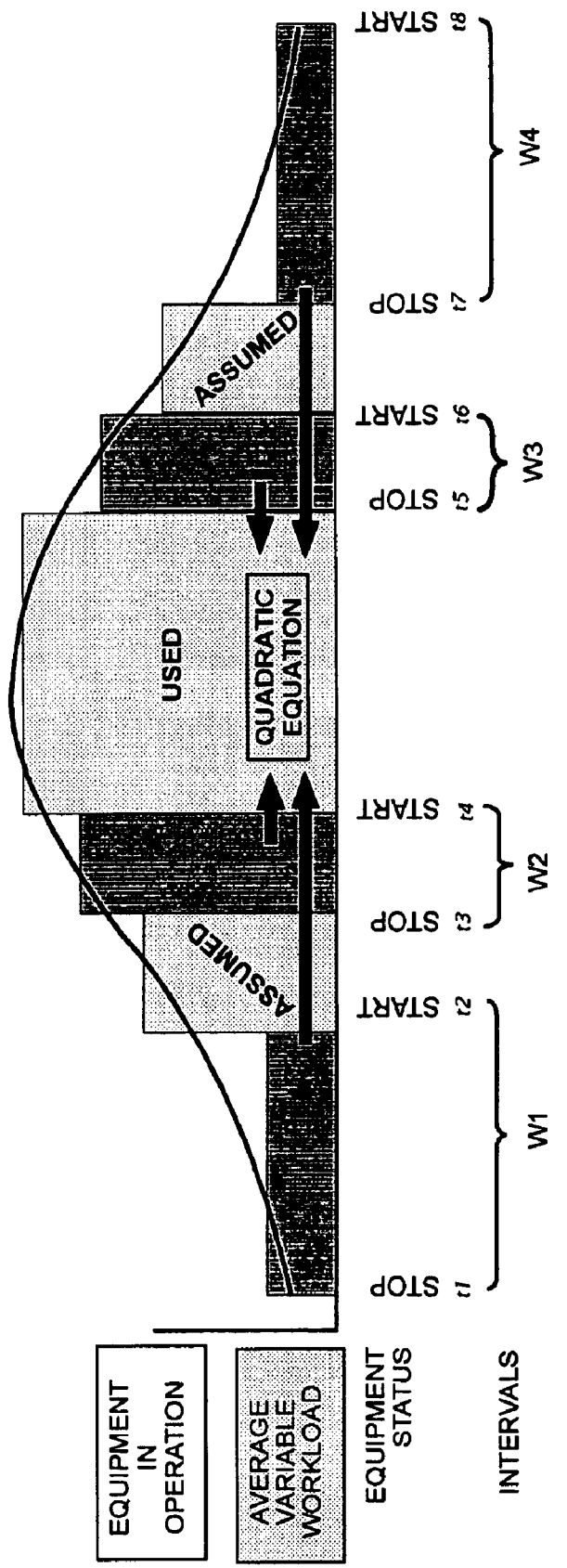
FIG. 6 is a graph of a cyclic equipment efficiency monitoring system with a work-load accumulation period and equipment-in-operation period according to an embodiment of the present invention.

Step B:

When Equation 3 is used on the 2 cycles immediately prior and after a period in which the equipment is in operation, then the workload for the period of operation of the equipment will be extracted from the function calculated with the 4 workloads and will be used to calculate the throughput for the period of operation of the equipment (FIG. 6).

This formula gives a function $f(t)$ in which the average of each intervals is equal to the workload used to calculate it. In which:

$$\int_{t1}^{t2} f(t)dt = W1, \int_{t3}^{t4} f(t)dt = W2,$$

$$\int_{t5}^{t6} f(t)dt = W3 \text{ and } \int_{t7}^{t8} f(t)dt = W4.$$

The function w(t), which is a curve with two possible changes of direction, is the following:

$$w(t) = at_3 + bt_2 + ct + d$$

Thus:

$$\int_{t1}^{t2} f(t)dt = \int_{t1}^{t2} at^3 + bt^2 + ct + d = a\int_{t1}^{t2} t^3 dt +$$

$$b\int_{t1}^{t2} t^2 dt + c\int_{t1}^{t2} t dt + d\int_{t1}^{t2} dt$$

$$= a\left[\frac{t^4}{4} + K_1\right]_{t1}^{t2} + b\left[\frac{t^3}{3} + K_2\right]_{t1}^{t2} + c\left[\frac{t^2}{2} + K_3\right]_{t1}^{t2} + d[t + K_4]_{t1}^{t2}$$

$$= a\left[\left(\frac{t2^4}{4} + K_1\right) + \left(\frac{t1^4}{4} + K_1\right)\right] + b\left[\left(\frac{t2^3}{3} + K_1\right) + \left(\frac{t1^3}{3} + K_1\right)\right] +$$

$$c\left[\left(\frac{t2^2}{2} + K_1\right) + \left(\frac{t1^2}{2} + K_1\right)\right] + d[(t2 + K_1) + (t1 + K_1)]$$

This gives the average workload for the first interval:

$$= a\left(\frac{t2^4 - t1^4}{4}\right) + b\left(\frac{t2^3 - t1^3}{3}\right) + c\left(\frac{t2^2 - t1^2}{2}\right) + d(t2 + t1) = W1$$

It is the same for the 3 other intervals:

$$= a\left(\frac{t4^4 - t3^4}{4}\right) + b\left(\frac{t4^3 - t3^3}{3}\right) + c\left(\frac{t4^2 - t3^2}{2}\right) + d(t4 + t3) = W2$$

$$= a\left(\frac{t6^4 - t5^4}{4}\right) + b\left(\frac{t6^3 - t5^3}{3}\right) + c\left(\frac{t6^2 - t5^2}{2}\right) + d(t6 + t5) = W3$$

$$= a\left(\frac{t8^4 - t7^4}{4}\right) + b\left(\frac{t8^3 - t7^3}{3}\right) + c\left(\frac{t8^2 - t7^2}{2}\right) + d(t8 + t7) = W4$$

It gives 4 equations with 4 unknowns that can be resolve to find the values of a, b, c and d of the function Workload(t) $=at_3+bt_2+ct+d$. The average workload for the period t4–t5 is $$\overline{\text{Workload}} = \int_{t4}^{t5} \text{workload}(t)dt$$

Figure 7:
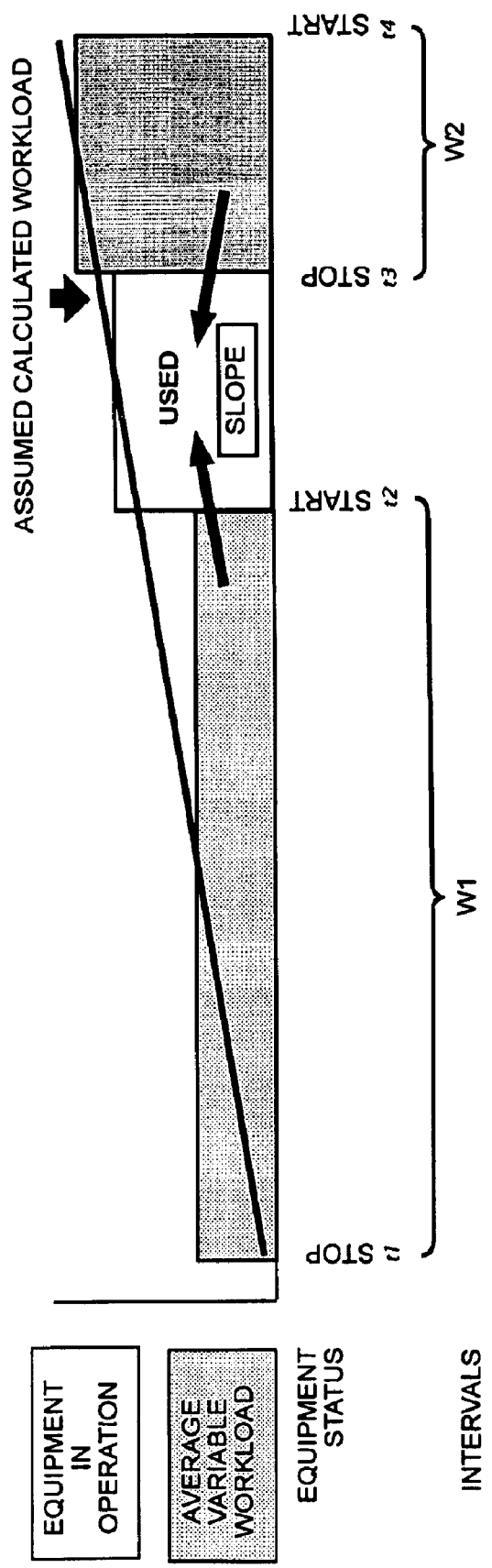
FIG. 7 is a graph of a cyclic equipment efficiency monitoring system with a work-load accumulation period and equipment-in-operation period according to an embodiment of the present invention.

Step C:

When Equation 3 is used immediately before and after a period in which the equipment is in operation and no other calculated workload are available immediately prior or immediately after those, then a slope of the two workloads calculated with Equation 3 will be assumed to calculate the efficiency of the equipment in operation for the period (FIG. 7).

$$ta = \frac{t2-t1}{2}$$

$$tb = \frac{t4-t1}{2} + \frac{t3-t1}{2}$$

$$tc = \frac{t3-t1}{2} + \frac{t2-t1}{2}$$

$$\text{Slope} = \frac{w2-w1}{tb-ta}$$

$$\overline{\text{Workload}} = W1 + \text{Slope} \times (tc-ta)$$

If the efficiency calculator is not powerful enough to use the quadratic equation, the average formula can be used but the accuracy of the results will be lower.

Figure 8:
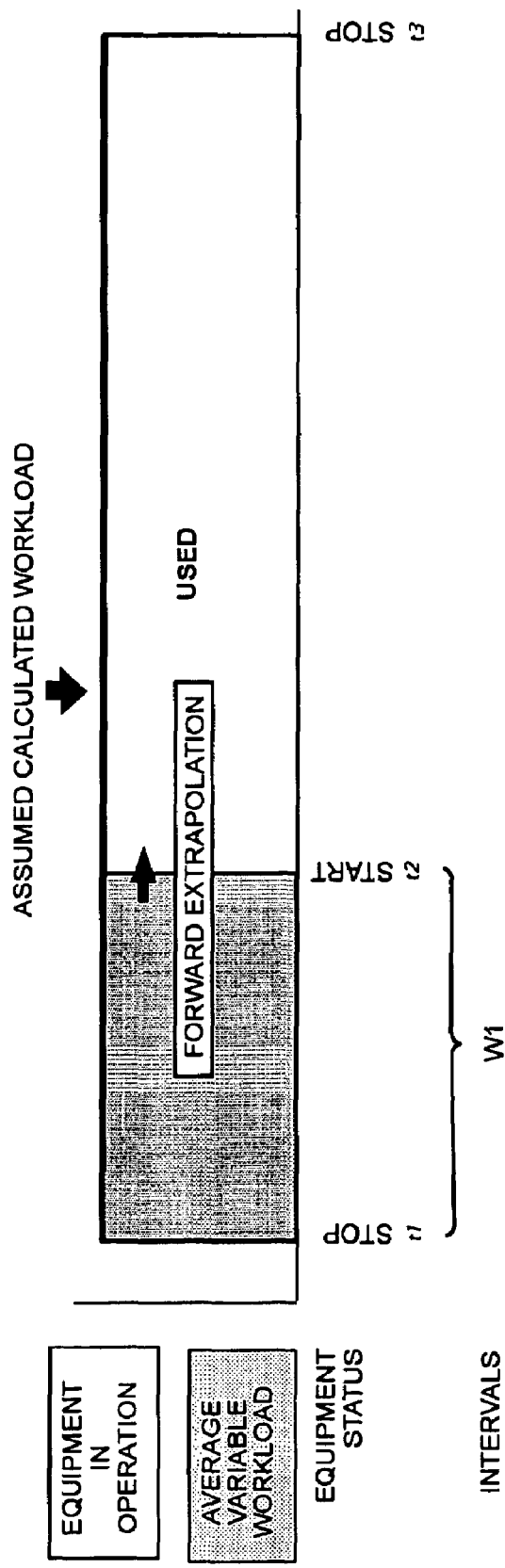
FIG. 8 is a graph of a cyclic equipment efficiency monitoring system with a work-load accumulation period and equipment-in-operation period according to an embodiment of the present invention.

Step D:

When Equation 3 is used immediately before but not after a period in which the equipment is in operation and no other calculated workload are available immediately prior, then the average variable workload can be extrapolated for the balance of the cycle (FIG. 8).

$$\overline{\text{Workload}} = W1$$

Figure 9:
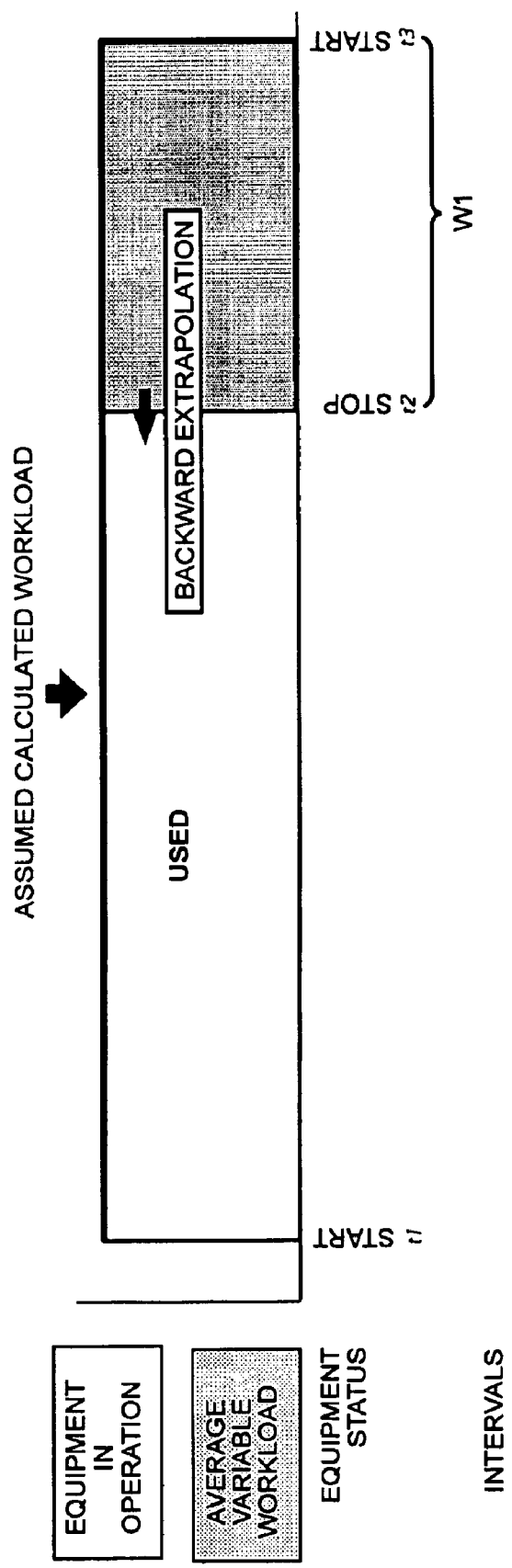
FIG. 9 is a graph of a cyclic equipment efficiency monitoring system with a work-load accumulation period and equipment-in-operation period according to an embodiment of the present invention.

Step E:

When Equation 3 is used immediately after but not before a period in which the equipment is in operation and no other calculated workload are available immediately after, then the average variable workload can be extrapolated backward within the last cycle (FIG. 9).

$$\overline{\text{Workload}} = W1$$

Figure 10:
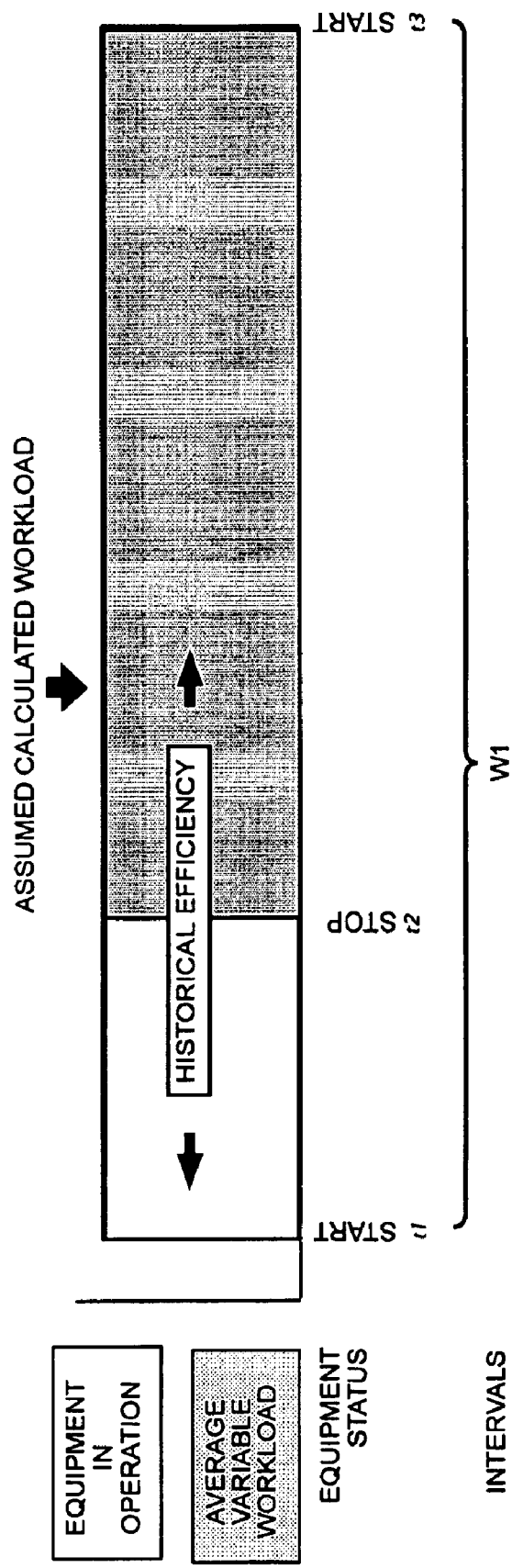
FIG. 10 is a graph of a cyclic equipment efficiency monitoring system with a work-load accumulation period and equipment-in-operation period according to an embodiment of the present invention.

Step F:

When Equation 3 can not be used immediately before or after a period in which the equipment is in operation and an historical efficiency is known, then the equipment's historical efficiency multiplied by the time of operation of the equipment for a period within a cycle divided by the time of the cycle gives the average variable workload within the cycle. (FIG. 10)

$$\overline{\text{Workload}} = \frac{\overline{\text{Efficiency}} \times (t2-t1)}{t3-t1} \quad \overline{\text{Workload}} = \frac{\overline{\text{Efficiency}} \times (t3-t2)}{t3-t1}$$

Formulas "A to F" (FIGS. 5–10) are elements of the workload calculator, which generate the most accurate workload based on available information.

Figure 11A:
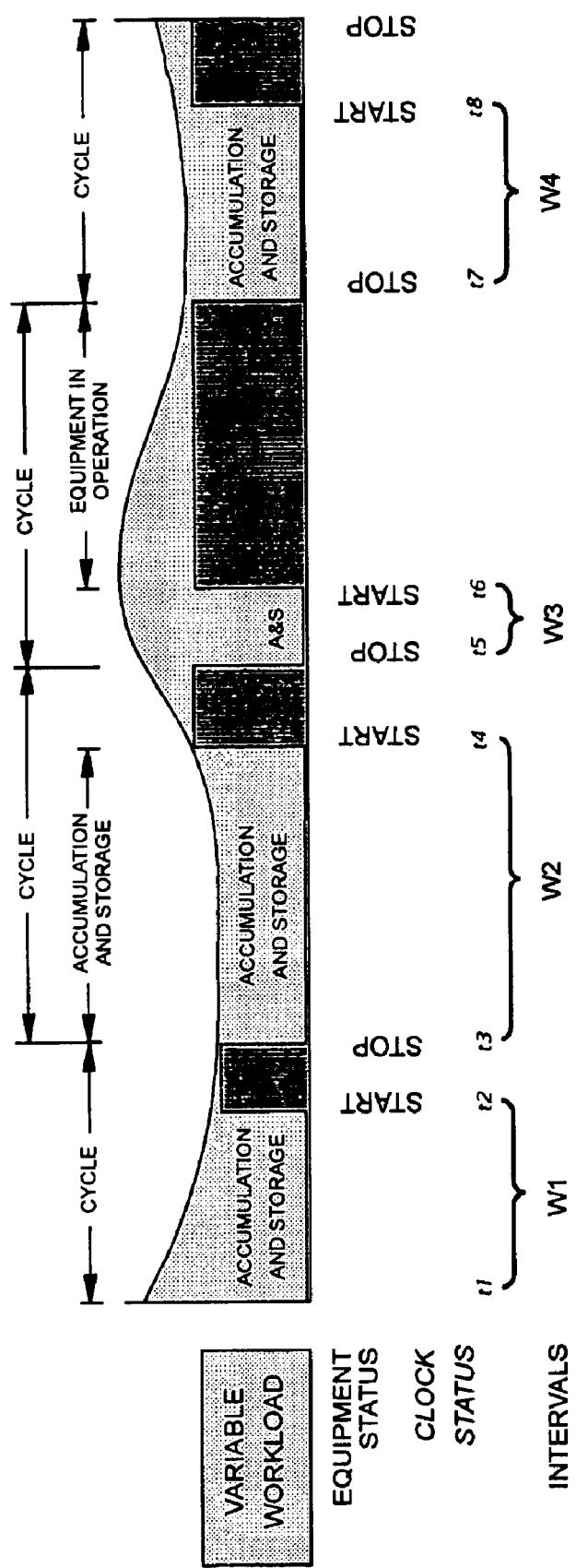
FIG. 11A is a graph of a cyclic equipment efficiency monitoring system with a work-load accumulation period and equipment-in-operation period according to an embodiment of the present invention.
Figure 11B:
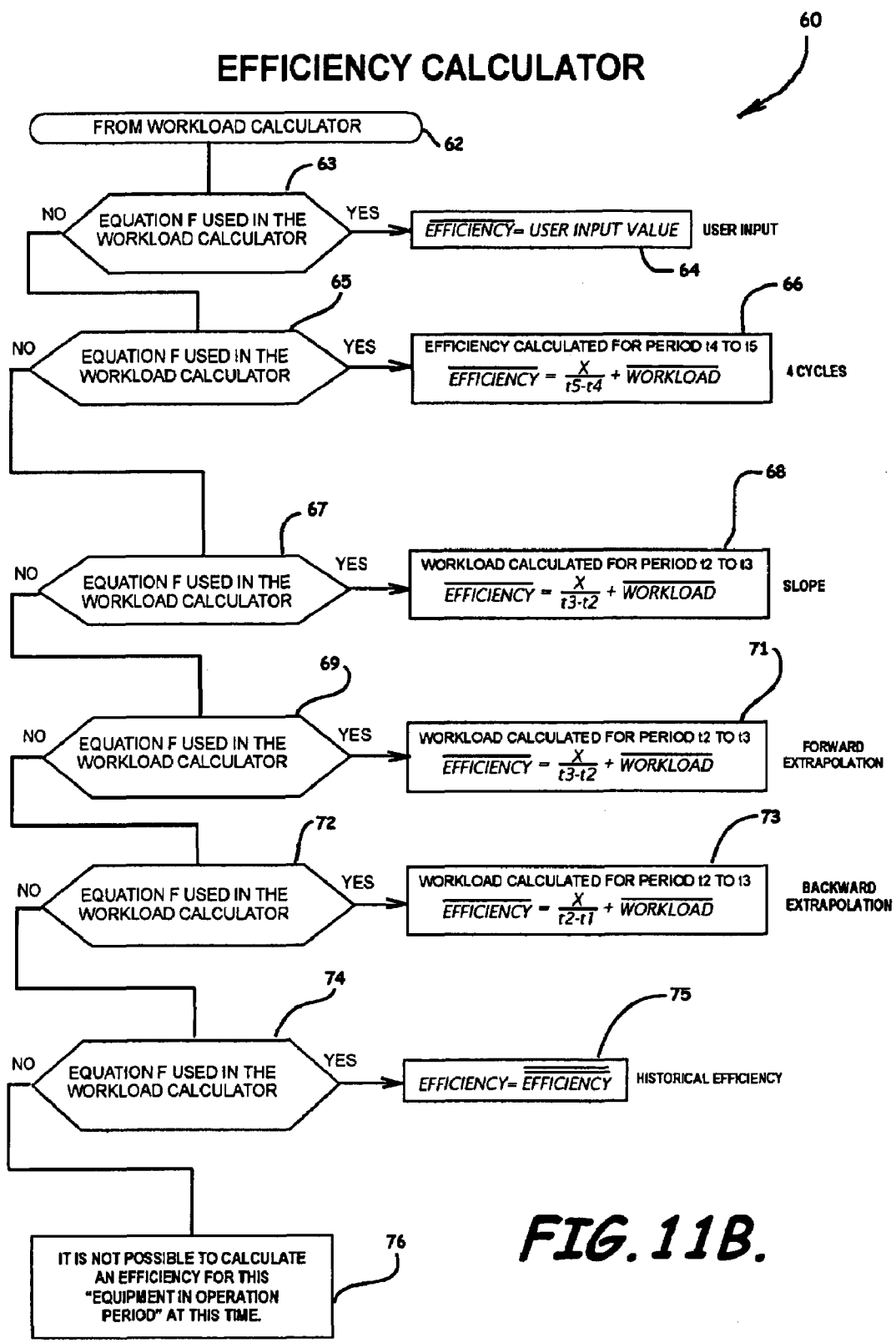
FIG. 11B is a flowchart of a graph of a cyclic equipment efficiency monitoring system with a work-load accumulation period and equipment-in-operation period according to an embodiment of the present invention.
Figure 13A:
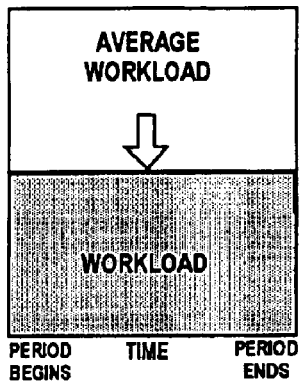
FIG. 13A is a graph of a cyclic equipment efficiency monitoring system with a work-load accumulation period and equipment-in-operation period according to an embodiment of the present invention.
Figure 13B:
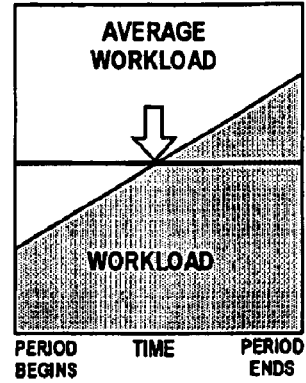
FIG. 13B is a graph of a cyclic equipment efficiency monitoring system with a work-load accumulation period and equipment-in-operation period according to an embodiment of the present invention.
Figure 13C:
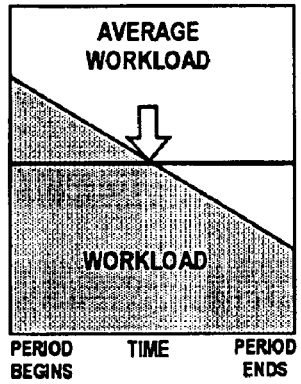
FIG. 13C is a graph of a cyclic equipment efficiency monitoring system with a work-load accumulation period and equipment-in-operation period according to an embodiment of the present invention.
Figure 13D:
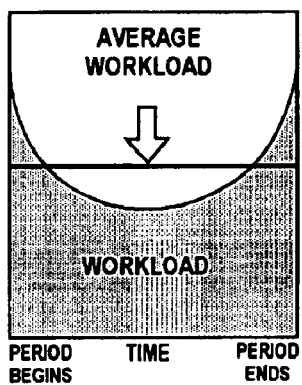
FIG. 13D is a graph of a cyclic equipment efficiency monitoring system with a work-load accumulation period and equipment-in-operation period according to an embodiment of the present invention.
Figure 13E:
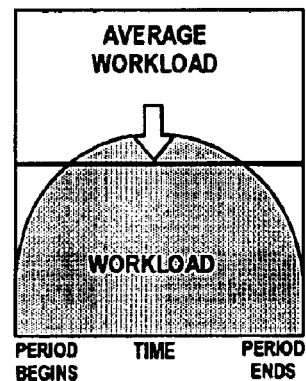
FIG. 13E is a graph of a cyclic equipment efficiency monitoring system with a work-load accumulation period and equipment-in-operation period according to an embodiment of the present invention.

Step G:

Now that the workload is known, it is time to calculate the efficiency. Therefore, as shown in Equation 2, if the operator enters a predetermined efficiency for a period, then the workload is calculated using this efficiency (FIG. 11).

If Step A or algorithm A (user input) is used, then:

$$\overline{\text{Efficiency}} = \text{User input value}$$

Note, in Steps or algorithms "H to L", described herein below, x represents a constant, which will never change unless the storage capacity related to the period calculated changes. Changing the accumulation and storage weight on a conveyor belt or changing the volume stored in a tank are examples of these. If this occurs, then x will get a new constant having no relation to the last one.

Step H:

If Step B (4 cycles) is used to determine average variable workload for period t4 to t5, then mean efficiency for period t4 to t5 is calculated as:

$$\overline{\text{Efficiency}} = \frac{x}{t5-t4} + \overline{\text{Workload}}$$

Step I:

If Sept C (slope or average) is used to determine average variable workload for:

$$\overline{\text{Efficiency}} = \frac{x}{t3-t2} + \overline{\text{Workload}}$$

Step J:

If Step D (forward extrapolation) is used, then:

$$\overline{\text{Efficiency}} = \frac{x}{t3-t2} + \overline{\text{Workload}}$$

Step K:

If Step E (backward extrapolation) is used, then:

$$\overline{\text{Efficiency}} = \frac{x}{t2-t1} + \overline{\text{Workload}}$$

Step L:

If Step F (Historical Efficiency) is used, then:

$$\overline{\text{Efficiency}} = \overline{\text{Efficiency}}$$

For each of the steps or algorithms "A to L", a workload and efficiency accuracy increment or self adjusting mechanism readjusts the variable workload and the equipment efficiency according to a variable tolerance of the difference between the historical efficiency of many cycles and the last cycle efficiency, and using this difference to readjust a variable tolerance. Even if, however, all the steps or algorithms "A to L" cover most of the probable workload behaviors. For example, there is always a possibility of some bizarre, but still relatively normal behaviours meaning that we could expect the workload to increase in the next period, but is does the opposite. FIG. 13 shows some of the more normal behaviors. Alone, they are all very normal. When joined, however, their behaviour could become confusing.

The efficiency of an equipment operating cyclically to displace a perpetual variable workload is directly influenced by the accumulated workload to be displaced when the equipment will be in operation. In a conveyor system, if pieces are falling on the conveyor belt at almost the same speed as they are displaced, then the conveyor motor will take more time to stop. This condition is called a lock-on phenomenon (FIG. 13). If the weight on the belt is low before the lock-on occurs, then the motor will be more efficient because there is less weight to be displaced. If the weight is high before the lock-on occurs, then the motor will be less efficient because there is more weight to be displaced. The lock-on phenomenon can generate high discrepancies between E$\overline{fficiency}$ and E$\overline{\overline{fficiency}}$. This is one of the reasons for using the Self Adjusting Mechanism.

Figure 14:
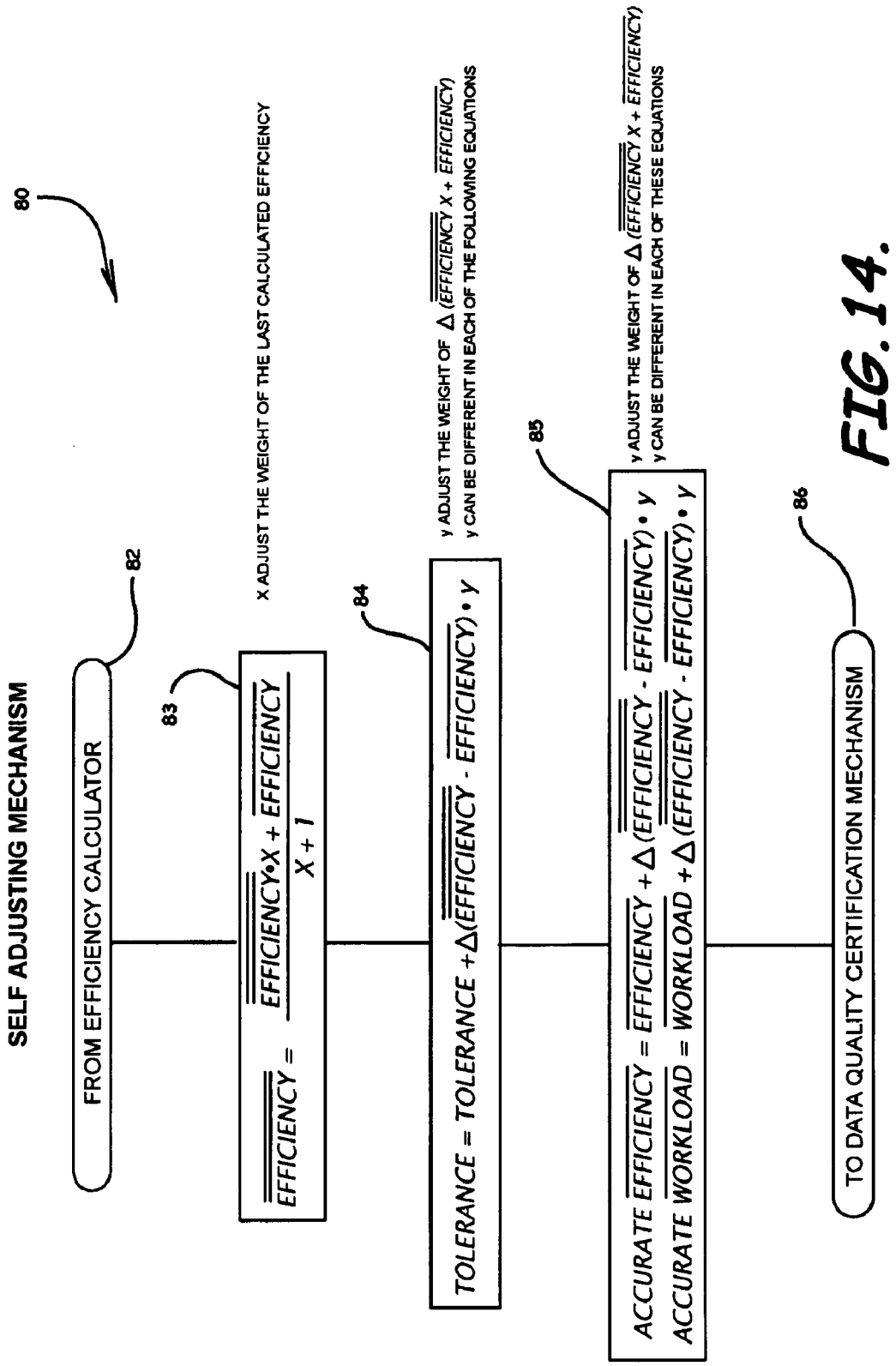
FIG. 14 is a flowchart of a cyclic equipment efficiency monitoring system with a work-load accumulation period and equipment-in-operation period according to an embodiment of the present invention.

Self Adjusting Mechanism optimizes accuracy according to each specific system (FIG. 14). To do this:

E$\overline{\overline{fficiency}}$ represents the average of a plurality of E$\overline{fficiency}$.

$$\overline{\overline{\text{Efficiency}}} = \frac{\overline{\overline{\text{Efficiency}}} \cdot x + \overline{\text{Efficiency}}}{x+1}$$

The tolerance is a normal and acceptable variation between the last calculated E$\overline{fficiency}$ and E$\overline{\overline{fficiency}}$. To adjust automatically this tolerance, the accuracy of E$\overline{\overline{fficiency}}$ must be optimum. This is why the tolerance is adjusted only when the 4 cycles algorithm (algorithm B) is used to calculate E$\overline{fficiency}$.

$$\text{Tolerance} = \text{Tolerance} + \Delta(\overline{\text{Efficiency}} - \overline{\overline{\text{Efficiency}}}) \cdot y$$

y represents the weight of the adjustment to the tolerance.

A variable tolerance refers to an acceptable percentage of difference between the E$\overline{fficiency}$ and the E$\overline{\overline{fficiency}}$. The variable tolerance is increased if E$\overline{fficiency}$ is too close to the limit of E$\overline{\overline{fficiency}}$±the variable tolerance or if it exceeds it. The variable tolerance is reduced if E$\overline{fficiency}$ is closer to E$\overline{\overline{fficiency}}$ than the limit of E$\overline{\overline{fficiency}}$±the variable tolerance. The E$\overline{fficiency}$ is used to update E$\overline{\overline{fficiency}}$. A proportion of accuracy factor is used to specify where the real efficiency is between E$\overline{fficiency}$ and E$\overline{\overline{fficiency}}$. The function Workload (t) is used to calculate at which average accumulated workload the E$\overline{fficiency}$ was calculated and change the proportion of accuracy factor accordingly. If the E$\overline{fficiency}$ calculated is within the range of E$\overline{\overline{fficiency}}$±the variable tolerance, then the proportion of accuracy factor will be different than if E$\overline{fficiency}$ was outside the variable tolerance. The proportion of accuracy is always applied to readjust the values of W$\overline{orkload}$ and E$\overline{fficiency}$ according to the following equations:

$$\text{Accurate } \overline{\text{Efficiency}} = \overline{\text{Efficiency}} + \Delta(\overline{\text{Efficiency}} - \overline{\overline{\text{Efficiency}}}) \cdot y$$

$$\text{Accurate } \overline{\text{Workload}} = \overline{\text{Workload}} + \Delta(\overline{\text{Efficiency}} - \overline{\overline{\text{Efficiency}}}) \cdot y$$

Abnormal equipment operations are confirmed when a predetermined or auto-adjustable number of possible abnormal equipment operations occurring in a row are detected by comparing the cycle's efficiency to the historical efficiency plus or minus the variable tolerance calculated in "M".

Figure 15:
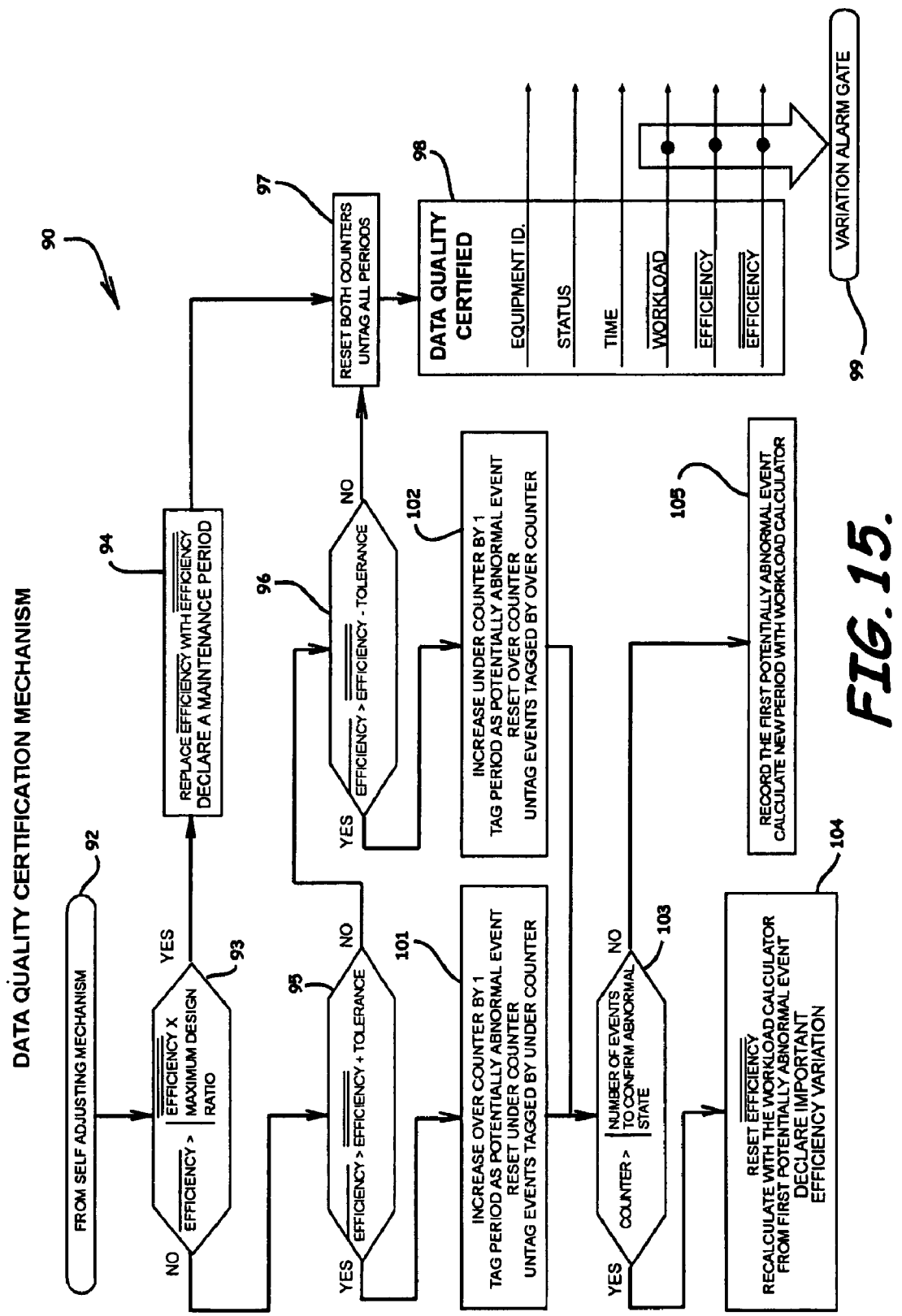
FIG. 15 is a flowchart of a cyclic equipment efficiency monitoring system with a work-load accumulation period and equipment-in-operation period according to an embodiment of the present invention.

The Self Adjusting Mechanism described in "M" gives accurate results if the system which the equipment is part of is operating normally, but the Self Adjusting Mechanism can not discern errors in calculation from abnormal equipment operation. A combination of counters and gates determines if the results, calculated when the equipment is in operation, are right or wrong (FIG. 15).

An event is composed of the equipment status, the time at which the equipment starts and stops, the W$\overline{orkload}$, the E$\overline{fficiency}$ and the E$\overline{\overline{fficiency}}$ for the period included between the start and stop time.

An under counter is increasing each time E$\overline{fficiency}$ is lower than E$\overline{\overline{fficiency}}$ minus the variable tolerance. When this occurs, the under counter tags the events used to calculate E$\overline{fficiency}$ as being possibly abnormal events.

An over counter is increasing each time E$\overline{fficiency}$ is higher than E$\overline{\overline{fficiency}}$ added to the variable tolerance. When this occurs, the over counter tags the events used to calculate E$\overline{fficiency}$ as being possibly abnormal events.

A reset means resets the under counter when the over counter increases, and resets the over counter when the under counter increases. It untags the possible abnormal events tagged by the under counter when the over counter increases, and untags the possible abnormal events tagged by the over counter when the under counter increases. It resets both counters and untags all possible abnormal events tagged by both counters when the E$\overline{fficiency}$ is within E$\overline{\overline{fficiency}}$±the variable tolerance.

A maintenance gate operates when E$\overline{fficiency}$ is higher than a predetermined maximum efficiency representing an efficiency ratio that could not be physically achieved under best conditions, like doubling the speed of an electric motor or doubling the throughput of a pump. When the E$\overline{fficiency}$ is higher than the predetermined maximum efficiency, it resets both counters (over and under) and untags the possible abnormal events tagged by both counters. It calculates the time of operation of the maintenance gate and the cumulative time of operation of the equipment during the operation of the maintenance gate. It calculates the total workload through the system using the E$\overline{\overline{fficiency}}$ multiplied by the time of operation of the equipment. It calculates the average workload for the time in which the maintenance gate is in operation by dividing the total workload through the system by the time of operation of the maintenance gate. Then it generates a maintenance status signal.

An abnormal event gate is used when one of the counters (over or under) increases. It operates when one of the counters is higher than a predetermined value representing the number of possible abnormal events necessary to become a confirmed abnormal events. It recalculates the E$\overline{\overline{fficiency}}$ from the time of the first tagged possible abnormal event then reprocesses the information recorded from the time of the first tagged possible abnormal event using the newly calculated E$\overline{\overline{fficiency}}$ when necessary. When the abnormal event gate is not in operation, it records the time of the first tagged possible abnormal event in its memory, and then tells the Workload Calculator to read a new event from the memory.

A maintenance status is declared for the period when the calculated efficiency is physically impossible. When this condition occurs, algorithm "L" is used to calculate the variable workload for that period.

Figure 16:
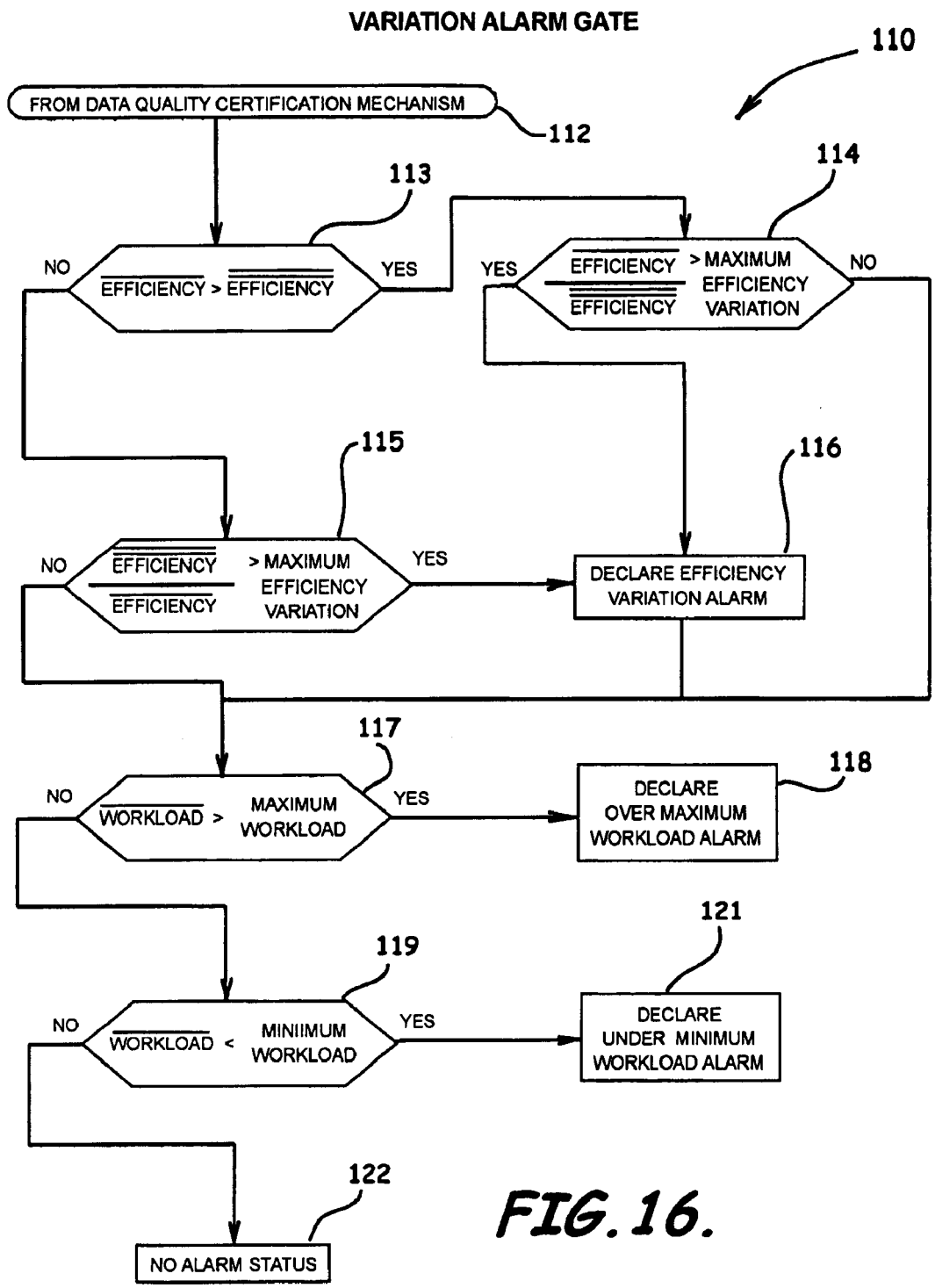
FIG. 16 is a flowchart of a cyclic equipment efficiency monitoring system with a work-load accumulation period and equipment-in-operation period according to an embodiment of the present invention.

Efficiency Variation Alarms are generated when the efficiency is over or under predetermined or auto-adjustable percentage variation (FIG. 16).

Workload Variation Alarms are generated when the workload is over or under predetermined or auto-adjustable percentage variation.

The embodiments of the present invention are related to a cyclic equipment efficiency monitoring system, software, and related methods. A cyclic equipment efficiency monitoring system, for example, includes a computer having memory defining an equipment efficiency monitoring server, efficiency monitoring software stored in the memory of the server, an area network in communication with the server, and an equipment monitor sensor, e.g., a current sensor, positioned remote from the server, in communication with the area network, and in communication with a cyclical equipment device to be monitored to sense on and off status of the cyclical equipment device and time that the cyclical equipment device is in the on status and in the off status. The equipment monitor sensor can also sense a cyclical equipment device identifier associated with the cyclical equipment device so that the cyclical equipment device being sensed by the equipment monitor sensor is specifically identified for monitoring.

The efficiency monitoring software, for example, includes a workload calculator responsive to the efficiency monitor sensor to calculate the workload of the cyclical equipment device and an efficiency calculator responsive to the workload calculator to determine the efficiency of the cyclical equipment device. The software can also include variations determiner responsive to the workload calculator and the efficiency calculator to determine a variation in the workload and the efficiency and a variation alarm initiator responsive to the variation determiner to initiate an alarm condition indicating that an abnormal variation has occurred. The variation determiner, for example, can include a tolerance comparator to compare a determined tolerance value with an acceptable value and a tolerance modifier responsive to the tolerance comparator and the efficiencies determined by the efficiency calculator to modify or adjust the tolerance. The tolerance comparator also can be in communication with the workload calculator to further enhance workload calculations when a potential abnormal variation is determined.

The cyclical equipment device, for example, can be a conveyor, a lift station, a water tower, or any other cyclical equipment. The system and software advantageously operate to monitor workload and efficiency, without the need for continuous operator input, complex sensor input, or specialized metering equipment, and to determine deterioration within the equipment being monitored. Rather than special sensors, meters, or continuous operator input, the system can utilize equipment status signals, e.g., on/off, and clock signals, e.g., length of time on and/or off, to effectively monitor the equipment. Also, the equipment status and time can be stored in the memory of server, if desired. The system, for example, does not need to sense or measure speed, volume, pressure, or weight per unit time. Instead, calculations of workload and efficiency are based on predetermined assumptions about the equipment from which the workload, efficiencies, and other calculations from status and time can be made.

In the drawings and specification, there have been disclosed typical preferred embodiments of the invention and, although specific terms are employed, they are used in a generic and descriptive sense only and not for the purpose of limitation.

What is claimed is:

1. A cyclic equipment efficiency monitoring system to remotely monitor a cyclical equipment device, comprising:

an equipment efficiency datacenter computer positioned at an equipment efficiency datacenter site to define an equipment efficiency monitoring server, the equipment efficiency monitoring server having memory associated therewith;

a database stored in the memory of the equipment efficiency monitoring server and having a plurality of cyclic equipment device records including a preselected maximum capable accumulated workload of a cyclical equipment device defining a cyclical equipment storage capacity, a predetermined manufacturer's cyclical equipment device maximum specification efficiency ratio defining a maximum design ratio;

an area network in communication with the equipment efficiency monitoring server;

an equipment on-off status detector positioned remote from the equipment efficiency monitoring server, in communication with the area network, and in communication with the cyclical equipment device to be remotely monitored to detect equipment on-off status; and efficiency monitoring software stored in the memory of the efficiency monitoring server, the software including:

a clocking generator positioned to generate a continuous running clock signal;

a data logger responsive to the clock signal and the equipment on-off status detector and positioned to log each time at which a change of status occurs in the cyclical equipment device and the equipment status at said time to thereby produce a plurality of time dependent equipment status entries, a first period of time between a first logged time when the equipment is in the off status and a second logged time when the equipment switches to the on status defining an equipment-accumulation-and-storage period and a second period of time between the second logged time and a third logged time when the equipment switches to the off status defining an equipment-in-operation period, the combination of the equipment-accumulation-and-storage period and the equipment-in-operation period defining an equipment cycle;

a workload estimator responsive to the data logger and positioned to estimate an average variable workload for a selected equipment-in-operation period, the average variable workload being an average workload accumulated and displaced by the cyclical equipment device as a function of a number of equipment-accumulation-and-storage periods and whether the equipment-accumulation-and-storage periods occur either prior-in-time or after-in-time with respect to the selected equipment-in-operation period;

an efficiency calculator responsive to the workload estimator and the data logger, positioned to retrieve the storage capacity of the cyclical equipment device from the database, and positioned to calculate a probable efficiency of the cyclical equipment device as a function of the average variable workload, the selected equipment-in-operation period, and the storage capacity of the cyclical equipment device for the selected equipment-in-operation period to thereby define an average efficiency, the average efficiency being an indicator of performance of the cyclical equipment device; and an accuracy incrementor including:
  an historical average efficiency determiner responsive to the efficiency calculator and a first historical average efficiency to determine a second historical average efficiency as a function of the average efficiency and the first historical average efficiency,
  a tolerance determiner responsive to the efficiency calculator, the historical average efficiency determiner, and a first variable tolerance, positioned to calculate a first weighted factor of a change in the difference between the historical average efficiency and average efficiency, and positioned to determine a second variable tolerance as a function of the first variable tolerance and the first weighted factor of change in the difference between the historical average efficiency and average efficiency,
  a workload accuracy incrementor responsive to the efficiency calculator, the workload determiner, and the tolerance determiner and positioned to increment average variable workload to reflect a second weighted factor of the change in the difference between the historical average efficiency and the average efficiency to define an incremented average variable workload, and
  an efficiency accuracy incrementor responsive to the efficiency calculator and the tolerance determiner and positioned to increment average efficiency to reflect a third weighted factor of the change in the difference between the historical average efficiency and average efficiency to define an incremented average efficiency; and a variation determiner including:
  a maintenance period determiner responsive to the historical average efficiency determiner and the efficiency accuracy incrementor, positioned to retrieve the maximum design ratio of the cyclical equipment device from the database, and positioned to determine if the incremented average efficiency is within a possible range of values defined as those not exceeding the product of the historical average efficiency and the maximum design ratio to thereby declare that a maintenance condition exists when such incremented average efficiency is outside the possible range of values;
  a tolerance comparator responsive to the maintenance period determiner, the average history determiner, and the tolerance determiner and positioned to compare the incremented average efficiency to at least one of a sum of the historical average efficiency and the variable tolerance to thereby detect an above tolerance condition and a difference between the historical average efficiency and the variable tolerance to thereby detect a below tolerance condition, the tolerance comparator further having:
    an under counter responsive to detection of the below tolerance condition and positioned to maintain and increase a count of time periods where the incremented average efficiency is below tolerance, and positioned to tag an associated reference equipment-in-operation time period used to calculate the incremented average efficiency as being a potentially abnormal event;
    an over counter responsive to detection of the above tolerance condition and positioned to maintain and increase a count of time periods where the incremented average efficiency is above tolerance, and positioned to tag an associated reference equipment-in-operation time period used to calculate the incremented average efficiency as being a potentially abnormal event; and
    a counter reset responsive to the under counter and over counter and responsive to reset the over counter and untag time periods tagged by the over counter when the under counter increases and positioned to reset the under counter and untag time periods tagged by the under counter when the over counter increases;
  an abnormal events counter responsive to the over counter and under counter and positioned to determine whether at least one of the over counter and the under counter exceed a preselected number of possible abnormal events, and when such condition exists, to thereby determine the existence of an abnormal state of operation of the cyclic equipment device; and
  an efficiency variation flag responsive to the abnormal events counter and positioned to declare a possible abnormal state of operation of the cyclical equipment device defining an important efficiency variation when the abnormal events counter determines that the at least one of the over counter and in the under counter exceed the preselected number of possible abnormal events.

2. A system of claim 1, wherein
the plurality of records in the database further include a preselected maximum allowable efficiency variation defining a maximum efficiency variation, a predetermined manufacturer's cyclical equipment device maximum specification workload defining a maximum workload, and a predetermined manufacturer's cyclical equipment device maximum specification minimum workload defining a minimum workload; and
the efficiency monitoring software further includes a variation alarm initiator responsive to the database, the workload accuracy incrementor, and the efficiency accuracy incrementor, and positioned to initiate an alarm condition indicating that an abnormal variation has occurred in at least one of the incremented average variable workload, the incremented average efficiency, and the historical average efficiency, and when such occurrence exists, to thereby notify the user of abnormal equipment behavior.

3. A method for monitoring a cyclic equipment device to monitor cyclic equipment efficiency, the method comprising the steps of:
sensing on a cyclical equipment device equipment status signals including on and off status of the cyclical equipment device, clock signals including time that the cyclical equipment device is in the on status and in the off status, and an equipment device identifier and so that the equipment device being sensed by the equipment monitor sensor is specifically identified for monitoring;

calculating an average variable workload signal representing workload being accumulated and displaced by the cyclical equipment device using the most accurate of an array of average variable workload algorithms; and calculating an efficiency signal representing efficiency of the cyclical equipment device for a cycle using the most accurate of an array of efficiency algorithms.

4. A method of claim 3, further comprising the step of:

optimizing accuracy of the workload signal and the efficiency signal by adjusting the workload and efficiency signals according to a proportion of accuracy factor whose value depends upon a variable tolerance and algorithm used by the efficiency calculator to calculate the efficiency.

5. A method of claim 4, further comprising the step of:

determining the quality of the optimized variable workload signal and optimized efficiency signal to verify that workload and efficiency values are within a possible range of values, so as to declare at least one of an alarm condition, a high variation condition, and a maintenance condition when outside the predetermined possible range of values.

6. A method of claim 5, further comprising the step of:

determining if the efficiency is within a predetermined maximum range of values, so as to declare a maintenance period where the efficiency exceeds the predetermined maximum value.

7. A method for monitoring a cyclic equipment device to monitor cyclic equipment efficiency, the method comprising the steps of:

counting periods with an under counter where an efficiency signal is lower than a difference of values of an historical efficiency signal and tolerance and where the signal is lower than the difference of the values of the historical efficiency signal and tolerance, tagging a period used to calculate the efficiency signal as being a possible abnormal event and resetting an over counter and untagging events tagged by the over counter; and counting periods where the efficiency signal is higher than a sum of values of the historical efficiency signal and tolerance with the over counter and where the signal is higher than the sum of the values of the historical efficiency signal and tolerance, tagging the period used to calculate the efficiency signal as being a possible abnormal event and resetting the under counter and untagging events tagged by the under counter.

8. A method of claim 6, further comprising the steps of:

determining whether either counter exceeds a number of possible abnormal periods necessary to confirm an abnormal state; and resetting the historical efficiency and declaring a very important efficiency variation condition to a user when either counter exceeds the number of possible abnormal periods necessary to confirm an abnormal state.

9. A method of claim 7, further comprising the step of:

increasing a number of time sample periods calculated by the workload calculator prior to releasing the workload signal when potentially abnormal events are detected.

10. A method of claim 8, further comprising the step of:

initiating an alarm condition indicating that an abnormal variation has occurred in at least one of the efficiency and workload where workload or the efficiency are outside acceptable limits.

11. A method of claim 9, further comprising the steps of:

declaring an efficiency variation alarm condition indicating an abnormal variation has occurred in at least one of the efficiency and workload where a ratio of at least one of the historical efficiency over the efficiency and the efficiency over the historical efficiency exceeds a maximum efficiency variation; and declaring a workload over maximum workload alarm when the average variable workload exceeds a maximum workload and declaring a workload under minimum alarm when the average variable workload is below a minimum workload.

* * * * *